United States Patent
O'Neill et al.

(10) Patent No.: US 9,265,566 B2
(45) Date of Patent: Feb. 23, 2016

(54) SURGICAL INSTRUMENT

(71) Applicant: COVIDIEN LP, Mansfield, MA (US)

(72) Inventors: Sean T. O'Neill, Los Gatos, CA (US); Jessica E. C. Olson, Frederick, CO (US)

(73) Assignee: Covidien LP, Mansfield, MA (US)

(*) Notice: Subject to any disclaimer, the term of this patent is extended or adjusted under 35 U.S.C. 154(b) by 196 days.

(21) Appl. No.: 14/043,322

(22) Filed: Oct. 1, 2013

(65) Prior Publication Data

US 2014/0107685 A1 Apr. 17, 2014

Related U.S. Application Data

(60) Provisional application No. 61/714,591, filed on Oct. 16, 2012.

(51) Int. Cl.
| | |
|---|---|
| A61B 17/32 | (2006.01) |
| A61B 18/14 | (2006.01) |
| A61B 17/29 | (2006.01) |
| A61B 19/00 | (2006.01) |

(52) U.S. Cl.
CPC ......... *A61B 18/1442* (2013.01); *A61B 18/1445* (2013.01); *A61B 18/1447* (2013.01); *A61B 2017/2901* (2013.01); *A61B 2017/292* (2013.01); *A61B 2017/2902* (2013.01); *A61B 2017/293* (2013.01); *A61B 2017/2929* (2013.01); *A61B 2018/1455* (2013.01); *A61B 2019/301* (2013.01)

(58) Field of Classification Search
CPC ............. A61B 17/28; A61B 17/29; A61B 2017/2902; A61B 17/295; A61B 2017/2929; A61B 2017/2932; A61B 18/1442; A61B 18/1445

USPC .......... 606/170, 205–207; 600/564; 227/134, 227/175.1–182.1, 19

See application file for complete search history.

(56) References Cited

U.S. PATENT DOCUMENTS

| | | |
|---|---|---|
| 2,801,633 A | 8/1957 | Ehrlich |
| 3,522,809 A | 8/1970 | Cornell |
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |

(Continued)

OTHER PUBLICATIONS

U.S. Appl. No. 08/926,869, filed Sep. 10, 1997, James G. Chandler.

(Continued)

*Primary Examiner* — Todd E Manahan
*Assistant Examiner* — Erich Herbermann

(57) ABSTRACT

A surgical instrument includes a housing and an elongated shaft having a distal portion and a proximal portion coupled to the housing. The elongated shaft defines a longitudinal axis and a mandrel at the proximal portion. An inner shaft member extends at least partially through the elongated shaft. An actuating mechanism is operably coupled to the mandrel and is configured to selectively cause movement of the elongated shaft in a longitudinal direction with respect to the inner shaft member. The surgical also includes an end effector that is adapted for treating tissue and includes an upper jaw member pivotally coupled to a distal portion of the inner shaft member about a pivot axis and a lower jaw member supported by the distal portion of the elongated shaft. Longitudinal movement of the elongated shaft is configured to pivot the upper jaw member relative to the lower jaw member.

5 Claims, 12 Drawing Sheets

(56) References Cited

U.S. PATENT DOCUMENTS

| | | |
|---|---|---|
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| 5,383,471 A | 1/1995 | Funnell |
| D358,887 S | 5/1995 | Feinberg |
| 5,445,638 A | 8/1995 | Rydell et al. |
| 5,462,546 A | 10/1995 | Rydell |
| 5,484,436 A | 1/1996 | Eggers et al. |
| 5,486,189 A | 1/1996 | Mudry et al. |
| 5,591,188 A | 1/1997 | Waisman |
| 5,611,813 A * | 3/1997 | Lichtman ............... 606/205 |
| D384,413 S | 9/1997 | Zlock et al. |
| 5,707,392 A | 1/1998 | Kortenbach |
| H1745 H | 8/1998 | Paraschac |
| 5,797,938 A | 8/1998 | Paraschac et al. |
| 5,800,449 A | 9/1998 | Wales |
| 5,807,393 A | 9/1998 | Williamson, IV et al. |
| 5,833,690 A | 11/1998 | Yates et al. |
| D402,028 S | 12/1998 | Grimm et al. |
| 5,849,022 A | 12/1998 | Sakashita et al. |
| D408,018 S | 4/1999 | McNaughton |
| 5,891,142 A | 4/1999 | Eggers et al. |
| 5,906,630 A | 5/1999 | Anderhub et al. |
| 5,911,719 A | 6/1999 | Eggers |
| 5,925,043 A | 7/1999 | Kumar et al. |
| 5,957,923 A | 9/1999 | Hahnen et al. |
| D416,089 S | 11/1999 | Barton et al. |
| 6,024,741 A | 2/2000 | Williamson, IV et al. |
| 6,041,679 A | 3/2000 | Slater et al. |
| D424,694 S | 5/2000 | Tetzlaff et al. |
| D425,201 S | 5/2000 | Tetzlaff et al. |
| 6,059,782 A | 5/2000 | Novak et al. |
| 6,117,158 A | 9/2000 | Measamer et al. |
| 6,123,701 A | 9/2000 | Nezhat |
| H1904 H | 10/2000 | Yates et al. |
| 6,149,794 A | 11/2000 | Heimann et al. |
| 6,206,877 B1 | 3/2001 | Kese et al. |
| 6,258,243 B1 | 7/2001 | Heimann et al. |
| 6,270,497 B1 | 8/2001 | Sekino et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| 6,443,952 B1 | 9/2002 | Mulier et al. |
| D465,281 S | 11/2002 | Lang |
| D466,209 S | 11/2002 | Bon |
| 6,669,695 B2 | 12/2003 | Luigi |
| 6,682,527 B2 | 1/2004 | Strul |
| D493,888 S | 8/2004 | Reschke |
| 6,776,780 B2 | 8/2004 | Mulier et al. |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| 6,964,662 B2 | 11/2005 | Kidooka |
| D525,361 S | 7/2006 | Hushka |
| 7,083,618 B2 | 8/2006 | Couture et al. |
| 7,090,673 B2 | 8/2006 | Dycus et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| D531,311 S | 10/2006 | Guerra et al. |
| 7,131,971 B2 | 11/2006 | Dycus et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al |
| D545,432 S | 6/2007 | Watanabe |
| D547,154 S | 7/2007 | Lee |
| 7,255,697 B2 | 8/2007 | Dycus et al. |
| D564,662 S | 3/2008 | Moses et al. |
| D567,943 S | 4/2008 | Moses et al. |
| 7,384,420 B2 | 6/2008 | Dycus et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,766,910 B2 | 8/2010 | Hixson et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| 8,070,748 B2 | 12/2011 | Hixson et al. |
| D661,394 S | 6/2012 | Romero et al. |
| 8,333,765 B2 | 12/2012 | Johnson et al. |
| 8,454,602 B2 | 6/2013 | Kerr et al. |
| 8,523,898 B2 | 9/2013 | Bucciaglia et al. |
| 8,529,566 B2 | 9/2013 | Kappus et al. |
| 8,568,408 B2 | 10/2013 | Townsend et al. |
| 8,591,510 B2 | 11/2013 | Allen, IV et al. |
| 8,628,557 B2 | 1/2014 | Collings et al. |
| 2002/0058925 A1 | 5/2002 | Kaplan et al. |
| 2002/0099373 A1* | 7/2002 | Schulze et al. .............. 606/51 |
| 2002/0188294 A1 | 12/2002 | Couture et al. |
| 2003/0018331 A1 | 1/2003 | Dycus et al. |
| 2003/0229344 A1 | 12/2003 | Dycus et al. |
| 2004/0087943 A1 | 5/2004 | Dycus et al. |
| 2009/0182327 A1 | 7/2009 | Unger |
| 2009/0209960 A1 | 8/2009 | Chojin |
| 2010/0082041 A1 | 4/2010 | Prisco |
| 2010/0094287 A1 | 4/2010 | Cunningham et al. |
| 2010/0179545 A1 | 7/2010 | Twomey et al. |
| 2011/0009864 A1 | 1/2011 | Bucciaglia et al. |
| 2011/0184405 A1 | 7/2011 | Mueller |
| 2011/0301592 A1 | 12/2011 | Kerr et al. |
| 2011/0301603 A1 | 12/2011 | Kerr et al. |
| 2012/0116433 A1* | 5/2012 | Houser et al. .............. 606/169 |
| 2012/0226276 A1 | 9/2012 | Dycus |
| 2012/0239034 A1 | 9/2012 | Horner et al. |
| 2012/0253344 A1 | 10/2012 | Dumbauld et al. |
| 2012/0259331 A1 | 10/2012 | Garrison |
| 2012/0265241 A1 | 10/2012 | Hart et al. |
| 2012/0283727 A1 | 11/2012 | Twomey |
| 2012/0283734 A1 | 11/2012 | Ourada |
| 2012/0296205 A1 | 11/2012 | Chernov et al. |
| 2012/0296238 A1 | 11/2012 | Chernov et al. |
| 2012/0296239 A1 | 11/2012 | Chernov et al. |
| 2012/0296317 A1 | 11/2012 | Chernov et al. |
| 2012/0296323 A1 | 11/2012 | Chernov et al. |
| 2012/0296324 A1 | 11/2012 | Chernov et al. |
| 2012/0296332 A1 | 11/2012 | Chernov et al. |
| 2012/0296333 A1 | 11/2012 | Twomey |
| 2012/0296334 A1 | 11/2012 | Kharin |
| 2012/0296371 A1 | 11/2012 | Kappus et al. |
| 2012/0303021 A1 | 11/2012 | Guerra et al. |
| 2012/0303025 A1 | 11/2012 | Garrison |
| 2012/0303026 A1 | 11/2012 | Dycus et al. |
| 2012/0310240 A1 | 12/2012 | Olson et al. |
| 2012/0316601 A1 | 12/2012 | Twomey |
| 2012/0323238 A1 | 12/2012 | Tyrrell et al. |
| 2012/0330308 A1 | 12/2012 | Joseph |
| 2012/0330309 A1 | 12/2012 | Joseph |
| 2013/0014375 A1 | 1/2013 | Hempstead et al. |
| 2013/0018364 A1 | 1/2013 | Chernov et al. |
| 2013/0018371 A1 | 1/2013 | Twomey |
| 2013/0018372 A1 | 1/2013 | Sims et al. |
| 2013/0022495 A1 | 1/2013 | Allen, IV et al. |
| 2013/0041370 A1 | 2/2013 | Unger |
| 2013/0041402 A1 | 2/2013 | Chojin et al. |
| 2013/0046295 A1 | 2/2013 | Kerr et al. |

(56) References Cited

U.S. PATENT DOCUMENTS

| | | |
|---|---|---|
| 2013/0046303 A1 | 2/2013 | Evans et al. |
| 2013/0046306 A1 | 2/2013 | Evans et al. |
| 2013/0046337 A1 | 2/2013 | Evans et al. |
| 2013/0060250 A1 | 3/2013 | Twomey et al. |
| 2013/0066303 A1 | 3/2013 | Hart |
| 2013/0066318 A1 | 3/2013 | Kerr |
| 2013/0071282 A1 | 3/2013 | Fry |
| 2013/0072919 A1 | 3/2013 | Allen, IV et al. |
| 2013/0072927 A1 | 3/2013 | Allen, IV et al. |
| 2013/0079760 A1 | 3/2013 | Twomey et al. |
| 2013/0079762 A1 | 3/2013 | Twomey et al. |
| 2013/0079774 A1 | 3/2013 | Whitney et al. |
| 2013/0082035 A1 | 4/2013 | Allen, IV et al. |
| 2013/0085491 A1 | 4/2013 | Twomey et al. |
| 2013/0085496 A1 | 4/2013 | Unger et al. |
| 2013/0085516 A1 | 4/2013 | Kerr et al. |
| 2013/0103030 A1 | 4/2013 | Garrison |
| 2013/0103031 A1 | 4/2013 | Garrison |
| 2013/0103035 A1 | 4/2013 | Horner et al. |
| 2013/0123837 A1 | 5/2013 | Roy et al. |
| 2013/0138101 A1 | 5/2013 | Kerr |
| 2013/0138102 A1 | 5/2013 | Twomey et al. |
| 2013/0138129 A1 | 5/2013 | Garrison et al. |
| 2013/0144284 A1 | 6/2013 | Behnke, II et al. |
| 2013/0150842 A1 | 6/2013 | Nau, Jr. et al. |
| 2013/0178852 A1 | 7/2013 | Allen, IV et al. |
| 2013/0185922 A1 | 7/2013 | Twomey et al. |
| 2013/0190753 A1 | 7/2013 | Garrison et al. |
| 2013/0190760 A1 | 7/2013 | Allen, IV et al. |
| 2013/0197503 A1 | 8/2013 | Orszulak |
| 2013/0218198 A1 | 8/2013 | Larson et al. |
| 2013/0226177 A1 | 8/2013 | Brandt et al. |
| 2013/0226178 A1 | 8/2013 | Brandt et al. |
| 2013/0232753 A1 | 9/2013 | Ackley et al. |
| 2013/0238016 A1 | 9/2013 | Garrison |
| 2013/0245623 A1 | 9/2013 | Twomey |
| 2013/0247343 A1 | 9/2013 | Homer et al. |
| 2013/0253489 A1 | 9/2013 | Nau, Jr. et al. |
| 2013/0255063 A1 | 10/2013 | Hart et al. |
| 2013/0267948 A1 | 10/2013 | Kerr et al. |
| 2013/0267949 A1 | 10/2013 | Kerr |
| 2013/0270322 A1 | 10/2013 | Scheib et al. |
| 2013/0274736 A1 | 10/2013 | Garrison |
| 2013/0282010 A1 | 10/2013 | McKenna et al. |
| 2013/0289561 A1 | 10/2013 | Waaler et al. |
| 2013/0296848 A1 | 11/2013 | Allen, IV et al. |
| 2013/0296854 A1 | 11/2013 | Mueller |
| 2013/0296856 A1 | 11/2013 | Unger et al. |
| 2013/0296922 A1 | 11/2013 | Allen, IV et al. |
| 2013/0296923 A1 | 11/2013 | Twomey et al. |
| 2013/0304058 A1 | 11/2013 | Kendrick |
| 2013/0304059 A1 | 11/2013 | Allen, IV et al. |
| 2013/0304066 A1 | 11/2013 | Kerr et al. |
| 2013/0310832 A1 | 11/2013 | Kerr et al. |
| 2013/0325057 A1 | 12/2013 | Larson et al. |
| 2013/0331837 A1 | 12/2013 | Larson |
| 2013/0338666 A1 | 12/2013 | Bucciaglia et al. |
| 2013/0338693 A1 | 12/2013 | Kerr et al. |
| 2013/0345701 A1 | 12/2013 | Allen, IV et al. |
| 2013/0345706 A1 | 12/2013 | Garrison |
| 2013/0345735 A1 | 12/2013 | Mueller |
| 2014/0005663 A1 | 1/2014 | Heard et al. |
| 2014/0005666 A1 | 1/2014 | Moua et al. |
| 2014/0025052 A1 | 1/2014 | Nau, Jr. et al. |
| 2014/0025053 A1 | 1/2014 | Nau, Jr. et al. |
| 2014/0025059 A1 | 1/2014 | Kerr |
| 2014/0025060 A1 | 1/2014 | Kerr |
| 2014/0025066 A1 | 1/2014 | Kerr |
| 2014/0025067 A1 | 1/2014 | Kerr et al. |
| 2014/0025070 A1 | 1/2014 | Kerr et al. |
| 2014/0025073 A1 | 1/2014 | Twomey et al. |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 13/085,144, filed Apr. 12, 2011, Keir Hart.
U.S. Appl. No. 13/483,733, filed May 30, 2012, Dennis W. Butcher.
U.S. Appl. No. 13/708,335, filed Dec. 7, 2012, Dumbauld.
U.S. Appl. No. 13/731,674, filed Dec. 31, 2012, Siebrecht.
U.S. Appl. No. 13/833,823, filed Mar. 15, 2013, Garrison.
U.S. Appl. No. 13/838,945, filed Mar. 15, 2013, Stoddard.
U.S. Appl. No. 13/903,091, filed May 28, 2013, Nau.
U.S. Appl. No. 13/903,116, filed May 28, 2013, Nau.
U.S. Appl. No. 13/903,223, filed May 28, 2013, Payne.
U.S. Appl. No. 14/017,572, filed Sep. 4, 2013, Arya.
U.S. Appl. No. 14/019,031, filed Sep. 5, 2013, Garrison.
U.S. Appl. No. 14/019,094, filed Sep. 5, 2013, Garrison.

* cited by examiner

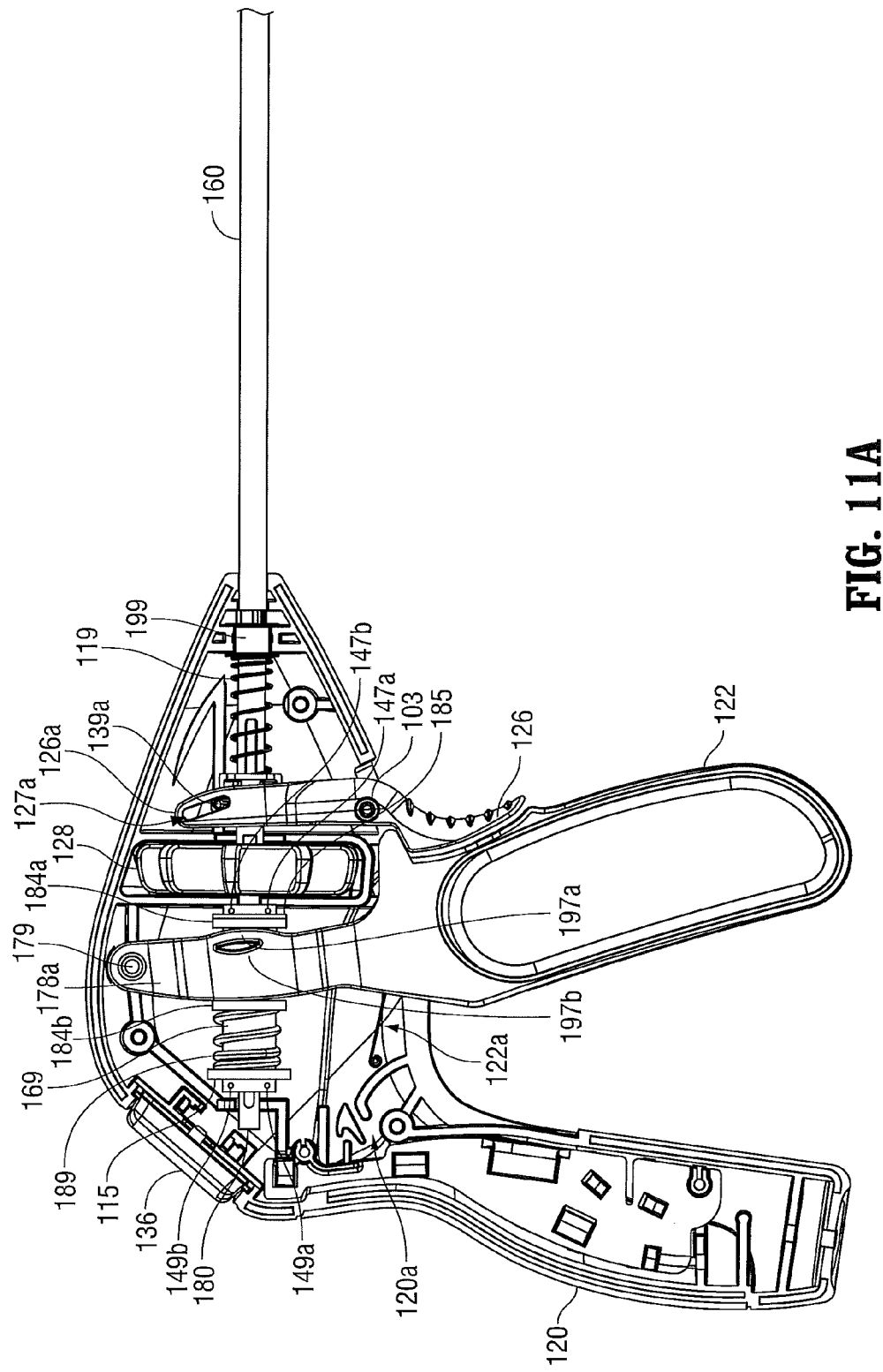

SURGICAL INSTRUMENT

CROSS REFERENCE TO RELATED APPLICATION

The present application claims the benefit of and priority to U.S. Provisional Application Ser. No. 61/714,591, filed on Oct. 16, 2012, the entire contents of which are incorporated herein by reference.

BACKGROUND

1. Technical Field

The present disclosure relates generally to the field of surgical instruments. In particular, the disclosure relates to an endoscopic electrosurgical forceps that is economical to manufacture and is capable of sealing and cutting relatively large tissue structures.

2. Background of Related Art

Instruments such as electrosurgical forceps are commonly used in open and endoscopic surgical procedures to coagulate, cauterize and seal tissue. Such forceps typically include a pair of jaws that can be controlled by a surgeon to grasp targeted tissue, such as, e.g., a blood vessel. The jaws may be approximated to apply a mechanical clamping force to the tissue, and are associated with at least one electrode to permit the delivery of electrosurgical energy to the tissue. The combination of the mechanical clamping force and the electrosurgical energy has been demonstrated to join adjacent layers of tissue captured between the jaws. When the adjacent layers of tissue include the walls of a blood vessel, sealing the tissue may result in hemostasis, which may facilitate the transection of the sealed tissue. A detailed discussion of the use of an electrosurgical forceps may be found in U.S. Pat. No. 7,255,697 to Dycus et al.

A bipolar electrosurgical forceps typically includes opposed electrodes disposed on clamping faces of the jaws. The electrodes are charged to opposite electrical potentials such that an electrosurgical current may be selectively transferred through tissue grasped between the electrodes. To effect a proper seal, particularly in relatively large vessels, two predominant mechanical parameters must be accurately controlled; the pressure applied to the vessel, and the gap distance established between the electrodes.

Both the pressure and gap distance influence the effectiveness of the resultant tissue seal. If an adequate gap distance is not maintained, there is a possibility that the opposed electrodes will contact one another, which may cause a short circuit and prevent energy from being transferred through the tissue. Also, if too low a force is applied the tissue may have a tendency to move before an adequate seal can be generated. The thickness of a typical effective tissue seal is optimally between about 0.001 and about 0.006 inches. Below this range, the seal may shred or tear and above this range the vessel walls may not be effectively joined. Closure pressures for sealing large tissue structures preferably fall within the range of about 3 kg/cm$^2$ to about 16 kg/cm$^2$.

As is traditional, the term "distal" refers herein to an end of the apparatus that is farther from an operator, and the term "proximal" refers herein to the end of the electrosurgical forceps that is closer to the operator.

SUMMARY

The present disclosure relates to an electrosurgical apparatus for electrosurgically sealing tissue. The present disclosure describes a surgical instrument for treating tissue that is economical to manufacture and is capable of sealing and cutting relatively large tissue structures.

The surgical instrument includes a housing and an elongated shaft having a distal portion and a proximal portion coupled to the housing. The elongated shaft defines a longitudinal axis and a mandrel at the proximal portion. An inner shaft member extends at least partially through the elongated shaft. An actuating mechanism is operably coupled to the mandrel and is configured to selectively cause movement of the elongated shaft in a longitudinal direction with respect to the inner shaft member. The surgical instrument also includes an end effector adapted for treating tissue. The end effector includes an upper jaw member pivotally coupled to a distal portion of the inner shaft member about a pivot axis and a lower jaw member supported by the distal portion of the elongated shaft. The elongated shaft is configured to pivot the upper jaw member relative to the lower jaw member upon longitudinal movement relative to the inner shaft member.

Additionally or alternatively, the elongated shaft may be configured to engage a foot extending from the upper jaw member such that longitudinal motion of the elongated shaft biases the foot to pivot the upper jaw member relative to the lower jaw member.

Additionally or alternatively, the elongated shaft may have a generally u-shaped profile including opposing interior sidewalls.

Additionally or alternatively, the inner shaft member may have a generally u-shaped profile including opposing interior sidewalls disposed laterally outward from the opposing interior sidewalls of the elongated shaft.

Additionally or alternatively, the surgical instrument includes a knife disposed between the opposing interior sidewalls of the elongated shaft and selectively movable in a longitudinal direction with respect to the elongated shaft.

Additionally or alternatively, the elongated shaft may be constructed from a single piece of metal.

Additionally or alternatively, the inner shaft member may be constructed from a single piece of metal.

According to another aspect of the present disclosure, a surgical instrument is provided. The surgical instrument includes a housing and an elongated shaft having a distal portion and a proximal portion coupled to the housing. The elongated shaft defines a longitudinal axis and a mandrel at the proximal portion. The elongated shaft has a generally u-shaped profile including opposing interior sidewalls. An inner shaft member extends at least partially through the elongated shaft. An actuating mechanism is operably coupled to the mandrel and is configured to selectively cause movement of the elongated shaft in a longitudinal direction with respect to the inner shaft member. The surgical instrument also includes an end effector adapted for treating tissue. The end effector includes an upper jaw member pivotally coupled to a distal portion of the inner shaft member about a pivot axis and a lower jaw member supported by the distal portion of the elongated shaft. The elongated shaft is configured to pivot the upper jaw member relative to the lower jaw member upon longitudinal movement relative to the inner shaft member. The surgical instrument also includes a knife extending at least partially through the elongated shaft between the opposing interior sidewalls. The knife is selectively movable in a longitudinal direction and includes a blade extendable through a tissue contacting portion of the jaw members.

Additionally or alternatively, the knife may be stamped from a single piece of metal.

Additionally or alternatively, the elongated shaft may be stamped from a single piece of metal.

Additionally or alternatively, the inner shaft member may be stamped from a single piece of metal.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

FIG. 11A is a side view of the proximal portion of the instrument of FIG. 8 depicting a movable handle in a separated position with respect to a stationary handle, which corresponds to the open configuration of the end effector depicted in FIG. 2A, and a knife trigger in a separated configuration with respect to the stationary handle, which corresponds to an un-actuated or proximal configuration of a knife with respect to the jaw members;

DETAILED DESCRIPTION

Figure 1:
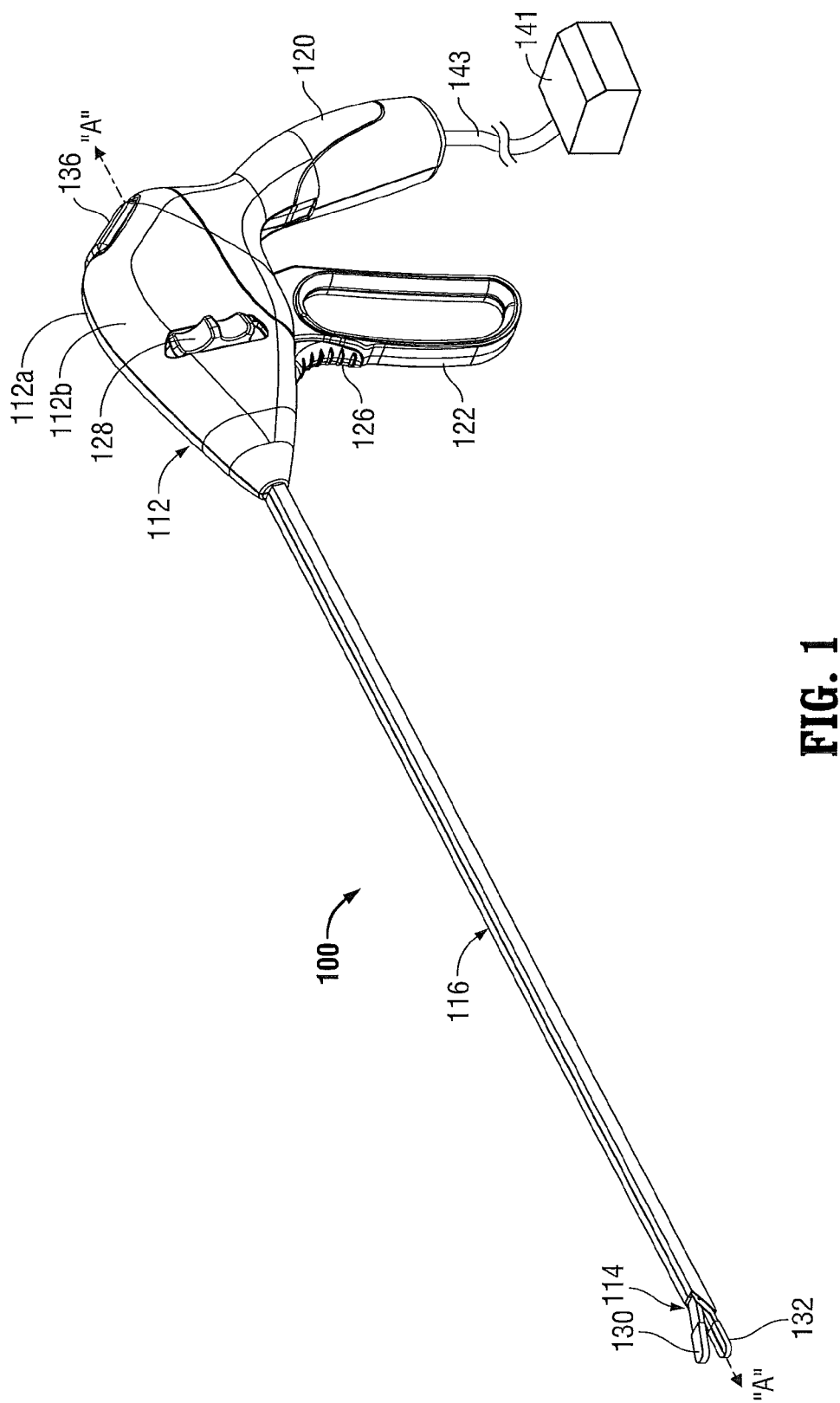
FIG. 1 is a perspective view of an electrosurgical forceps according to an embodiment of the present disclosure including a housing, an elongated shaft, and an end effector.

Referring initially to FIG. 1, an embodiment of an electrosurgical forceps 100 generally includes a housing 112 that supports various actuators thereon for remotely controlling an end effector 114 through an elongated shaft 116. Although this configuration is typically associated with instruments for use in laparoscopic or endoscopic surgical procedures, various aspects of the present disclosure may be practiced with traditional open instruments and in connection with endoluminal procedures as well.

The housing 112 is constructed of a left housing half 112a and a right housing half 112b. The left and right designation of the housing halves 112a, 112b refer to the respective directions as perceived by an operator using the forceps 100. The housing halves 112a, 112b may be constructed of sturdy plastic, and may be joined to one another by adhesives, ultrasonic welding or other suitable assembly methods.

To mechanically control the end effector 114, the housing 112 supports a stationary handle 120, a movable handle 122, a trigger 126 and a rotation knob 128. The movable handle 122 is operable to move the end effector 114 between an open configuration (FIG. 2A) wherein a pair of opposed jaw members 130, 132 are disposed in spaced relation relative to one another, and a closed or clamping configuration (FIG. 2B) wherein the jaw members 130, 132 are closer together. Approximation of the movable handle 122 with the stationary handle 120 serves to move the end effector 114 to the closed configuration and separation of the movable handle 122 from the stationary handle 120 serves to move the end effector 114 to the open configuration. The trigger 126 is operable to extend and retract a knife blade 156 (FIG. 2A) through the end effector 114 when the end effector 114 is in the closed configuration. The rotation knob 128 serves to rotate the elongated shaft 116 and the end effector 114 about a longitudinal axis A-A extending through the forceps.

To electrically control the end effector 114, the housing 112 supports a switch 136 thereon, which is operable by the user to initiate and terminate the delivery of electrosurgical energy to the end effector 114. The switch 136 is in electrical communication with a source of electrosurgical energy such as electrosurgical generator 141 or a battery (not shown) supported within the housing 112. The generator 141 may include devices such as the LIGASURE® Vessel Sealing Generator and the Force Triad® Generator as sold by Covidien Energy-based Devices of Boulder, Colo. A cable 143 extends between the housing 112 and the generator 141 and may include a connector (not shown) thereon such that the forceps 100 may be selectively coupled and decoupled electrically from the generator 141.

Figure 2A:
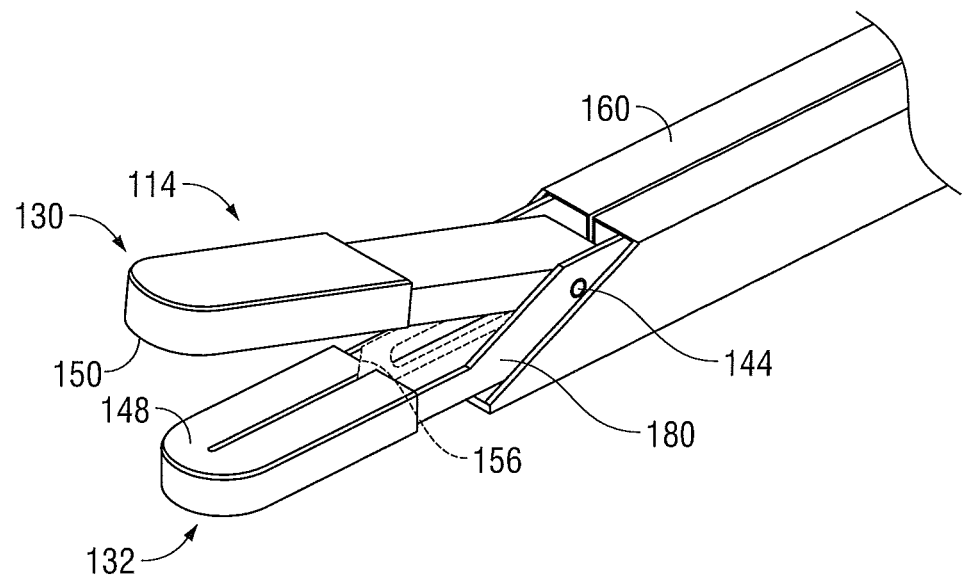
FIG. 2A is an enlarged perspective view of the end effector of FIG. 1 depicted with a pair of jaw members in an open configuration.
Figure 2B:
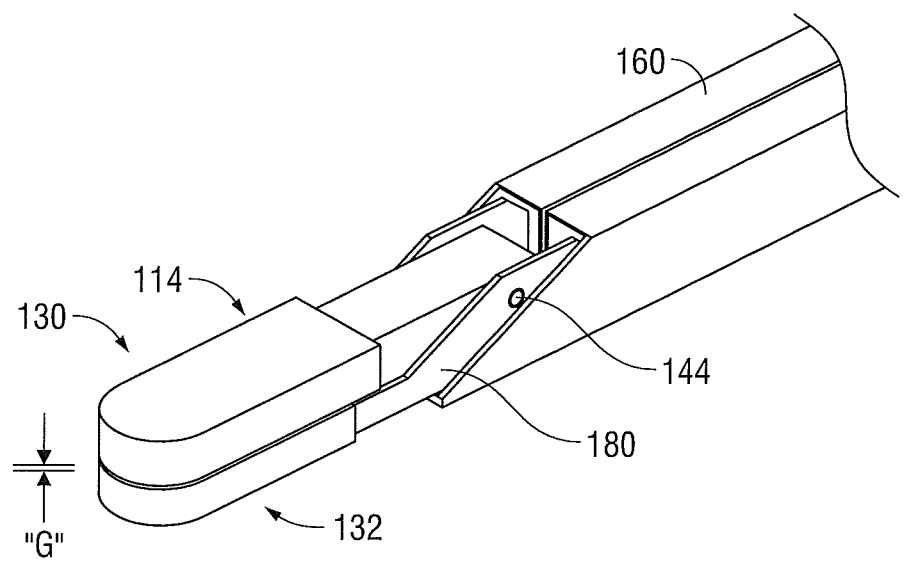
FIG. 2B is an enlarged perspective view of the end effector of FIG. 1 depicted with the pair of jaw members in a closed configuration.
Figure 3:
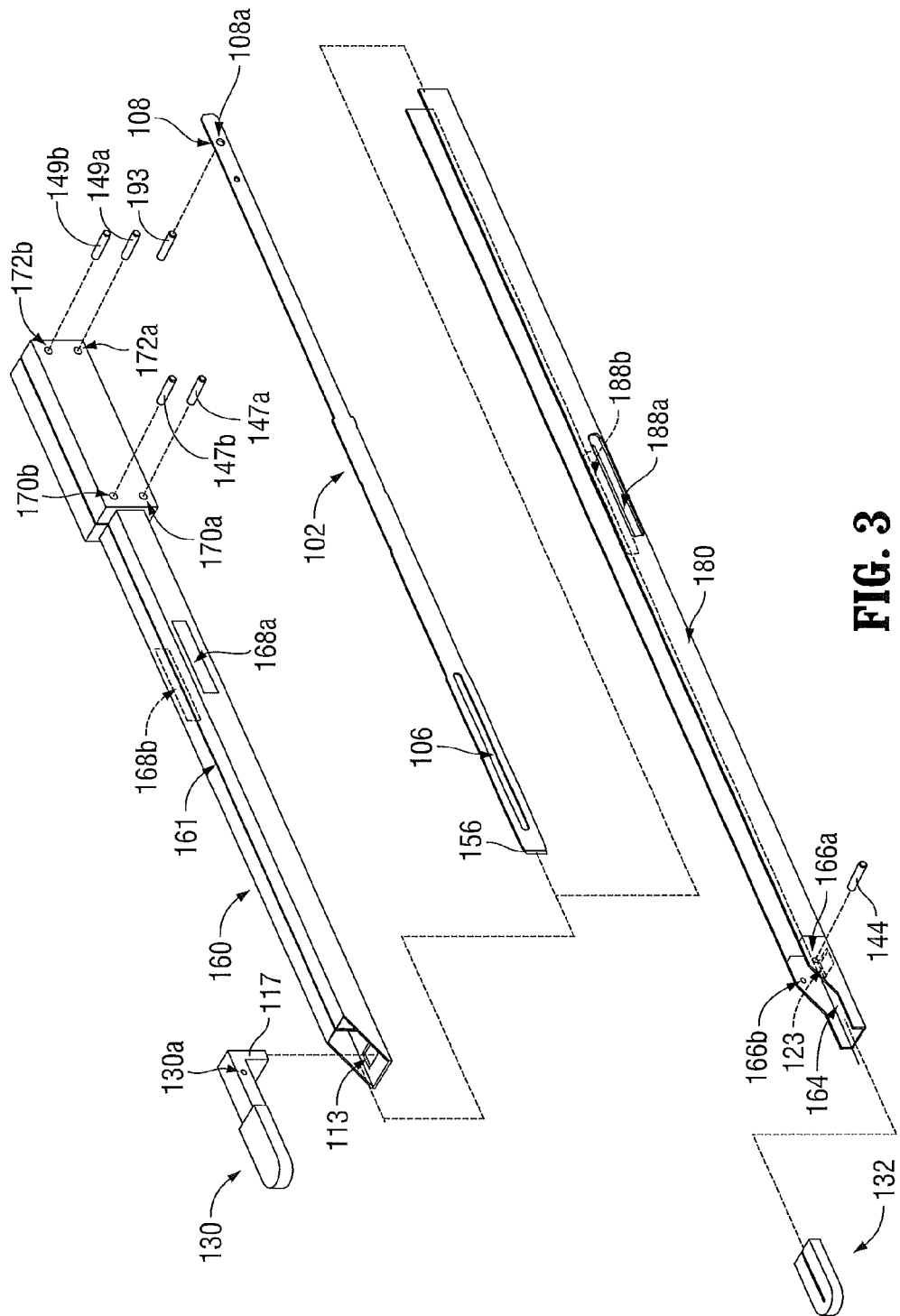
FIG. 3 is a perspective view of the end effector and elongated shaft of FIG. 1 with parts separated.

Referring now to FIGS. 2A-3, the end effector 114 may be moved from the open configuration (FIG. 2A) wherein tissue (not shown) is received between the jaw members 130, 132, and the closed configuration (FIG. 2B), wherein the tissue is clamped and sealed. The upper and lower jaw members 130, 132 are electrically coupled to cable 143, and thus to the generator 141 (e.g., via a respective wire extending through the elongated shaft 116) to provide an electrical pathway to a pair of electrically conductive, tissue-engaging sealing plates 148, 150 disposed on the lower and upper jaw members 132, 130, respectively. The sealing plate 148 of the lower jaw member 132 opposes the sealing plate 150 of the upper jaw member 130, and, in some embodiments, the sealing plates 148 and 150 are electrically coupled to opposite terminals, e.g., positive or active (+) and negative or return (−) terminals associated with the generator 141. Thus, bipolar energy may be provided through the sealing plates 148 and 150. Alternatively, the sealing plates 148 and 150 and/or the end effector 114 may be configured for delivering monopolar energy to the tissue. In a monopolar configuration, the one or both sealing plates 148 and 150 deliver electrosurgical energy from an active terminal, e.g. (+), while a return pad (not shown) is placed generally on a patient and provides a return path to the opposite terminal, e.g. (−), of the generator 141.

Figure 5:
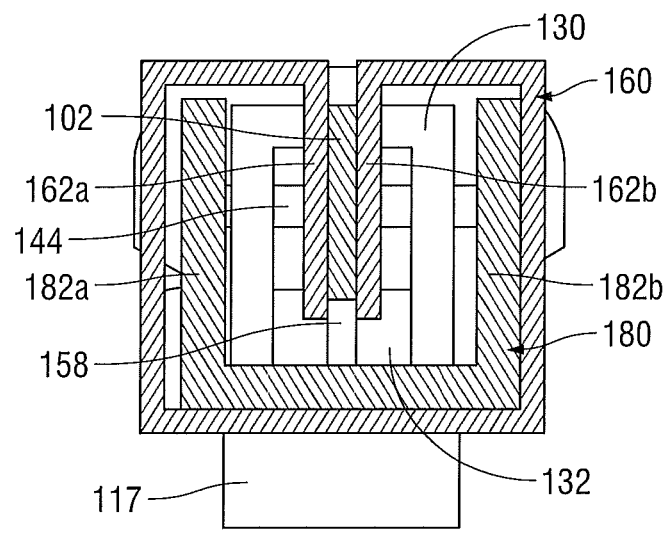
FIG. 5 is a cross-sectional, perspective view of the end effector assembled with the elongated shaft of FIG. 1.

Referring now to FIG. 3, the elongated shaft 116 includes various longitudinal components that operatively couple the end effector 114 to the various actuators supported by the housing 112 (FIG. 1). An outer shaft member 160 defines an exterior surface of the elongated shaft 116 and includes a mandrel 169 formed on a proximal portion thereof. As described in further detail below, mandrel 169 supports various components disposed within housing 112 that cooperate with the movable handle 122 to effect longitudinal movement of the outer shaft member 160 along the longitudinal axis A-A. The outer shaft member 160 generally exhibits a U-shaped profile including interior sidewalls 162a, 162b (FIG. 5). An inner shaft member 180 is received within the outer shaft member 160. Upper jaw member 130 is mechanically coupled to the inner shaft member 180 about a pivot pin 144. The pivot pin 144 extends through a throughbore 130a disposed through a proximal portion of jaw member 130 to pivotally support jaw member 130 at the distal end of the inner shaft member 180. Outer shaft member 160 is configured for longitudinal motion with respect to the inner shaft member 180.

The outer shaft member 160, including the mandrel 169, may be constructed from a single flat stock piece of metal. In constructing the outer shaft member 160, a stamping, punching or similar metal-working process may be employed to initially generate a flat blank that includes an appropriate outer profile and any interior openings or features. Thereafter, the necessary bends and curves may be formed by bending the flat blank with a press brake, or other suitable metal-working equipment. The outer shaft member 160 may be formed by folding the flat blank into a generally rectangular profile (or generally circular profile) such that two opposing longitudinal edges of the flat blank meet at a longitudinal seam 161 (FIG. 3). Although the longitudinal seam does not necessarily require joining by a mechanical interlock or any other suitable process, the seam may, in some embodiments, be joined by laser welding (or other suitable process) to form a continuous circular or other geometric (e.g., rectangular) profile. The seam may be generally straight, or alternatively, a box joint, a dovetail joint, or any other suitable interface known in the metal-working arts. Inner shaft member 180 may also be constructed and/or formed from a flat stock piece of metal substantially as described above with respect to outer shaft member 160.

At least a portion of the inner shaft member 180 extends distally from a distal end of the outer shaft member 160. An opening 164 at a distal end of the inner shaft member 180 is defined by opposing vertical sidewalls 164a and 164b. Sidewalls 164a, 164b include respective bores 166a, 166b extending therethrough to support the pivot pin 144 and maintain an orientation of the pivot pin 144 with respect to the outer shaft member 160. The pivot pin 144 may be frictionally supported by the bores 166a, 166b or fastened to the inner shaft member 180 by a laser or heat-based welding, adhesives, chemical bonding, or other suitable manufacturing processes.

A proximal portion of the upper jaw member 130 includes a foot member 117 that extends from the upper jaw member 130 to slide-fit through a window 113 disposed through a distal end of the outer shaft member 160 and a window 123 disposed through a distal end of the inner shaft member 180. Proximal longitudinal motion of the outer shaft member 160 causes the window 113 of the outer shaft member 160 to bias the foot member 117 proximally, thereby rotating the upper jaw member 130 about pivot pin 144 toward the lower jaw member 132 to the closed configuration (FIG. 2B). During rotation of the upper jaw member 130, the foot member 117 is free to move through the window 123 of the inner shaft member 180. The outer shaft member 160 may be drawn proximally relative to the pivot pin 144 to move the end effector 114 to the closed configuration (see FIG. 2B). Since the longitudinal position of the pivot pin 144 is fixed (by the inner shaft member 180), proximal retraction of the outer shaft member 160 causes the window 113 to bias the foot member 117 proximally, thereby pivoting the upper jaw member 130 about pivot pin 144 toward the lower jaw member 132 to the closed configuration (FIG. 2B). Conversely, when the end effector 114 is in the closed configuration, longitudinal translation of the outer shaft member 160 in a distal direction causes the window 113 to bias the foot member 117 proximally, thereby pivoting the upper jaw member 130 about pivot pin 144 away from jaw member 132 toward the open configuration (FIG. 2A).

The jaw members 130, 132 may be pivoted about the pivot pin 144 to move the end effector 114 to the closed configuration of FIG. 2B wherein the sealing plates 148, 150 provide a pressure to tissue grasped therebetween. In some embodiments, to provide an effective seal, a pressure within a range between about 3 kg/cm$^2$ to about 16 kg/cm$^2$ and, desirably, within a working range of 7 kg/cm$^2$ to 13 kg/cm$^2$ is applied to the tissue. Also, in the closed configuration, a separation or gap distance "G" may be maintained between the sealing plates 148, 150 by an array of stop members 154 (FIG. 2A) disposed on or adjacent the sealing plates 148, 150. The stop members 154 contact opposing surfaces on the opposing jaw member 130, 132 and prohibit further approximation of the sealing plates 148, 150. In some embodiments, to provide an effective tissue seal, an appropriate gap distance of about 0.001 inches to about 0.010 inches and, desirably, between about 0.002 and about 0.005 inches may be provided. In some embodiments, the stop members 154 are constructed of an electrically non-conductive plastic or other material molded onto the jaw members 130, 132, e.g., by a process such as overmolding or injection molding. In other embodiments, the stop members 154 are constructed of a heat-resistant ceramic deposited onto the jaw members 130, 132.

Electrosurgical energy may be delivered to the tissue through the electrically conductive seal plates 148, 150 to effect a tissue seal. Once a tissue seal is established, a knife blade 156 may be advanced through a knife channel 158 defined in one or both jaw members 130, 132 to transect the sealed tissue. Knife blade 156 is depicted in FIG. 2A as extending from the elongated shaft 116 when the end effector 114 is in an open configuration. In some embodiments, a knife lockout is provided to prevent extension of the knife blade 156 into the knife channel 158 when the end effector 114 is in the open configuration.

At a proximal portion of the outer shaft member 160, various features are provided that serve to couple the outer shaft member 160 to various elements of the housing 112. More specifically, the proximal portion of the outer shaft member 160 includes, in order from distal to proximal, a series of tabs 187 extending therefrom that serve to aid in securing the proximal portion of the outer shaft member 160 within the housing 112, a pair of opposing longitudinal slots 168a, 168b defined therethrough to allow longitudinal translation of a dowel pin 193 through the outer shaft member 160, and the mandrel 169. The mandrel 169 includes a distal set of through bore pairs 170a, 170b configured to receive a pair of stop pins 147a, 147b, respectively, and a proximal set of through bores 172a, 172b configured to receive a pair of stop pins 149a, 149b. The outer shaft member 160 may also include a suitable mechanical interface (not shown) configured to couple the outer shaft member 160 to the rotation knob 128. One example of a connection established between the outer shaft member 160 and the rotation knob 128 is described in the commonly-assigned patent application entitled SURGICAL INSTRUMENT WITH STAMPED DOUBLE-FLAG JAWS (application Ser. No. 13/461,335 filed May 1, 2012).

A proximal portion of the inner shaft member 180 includes a pair of opposing longitudinal knife slots 188a, 188b extending therethrough and configured to axially align with the pair of opposing longitudinal slots 168a, 168b defined through the outer shaft member 160 to allow longitudinal translation of the dowel pin 193 therethrough.

The knife 102 is a generally flat, metal component defining a profile that may be constructed by a stamping process. The knife 102 supports the sharpened knife blade 156 at a distal-most end thereof. The sharp edge of the knife blade 156 may be applied to the distal end of the knife 102 subsequent to the stamping process that forms the profile. For example, various manufacturing techniques may be employed such as grinding, coining, electrochemical etching, electropolishing, or other suitable manufacturing processes, for forming sharpened edges. A longitudinal slot 106 is defined within the knife 102 to provide clearance for the pivot pin 144. A proximal through bore 108a extends through a proximal portion 108 of the knife 102 and provides a mechanism for operatively coupling the knife 102 to the trigger 126 via the dowel pin 193. The connection between the knife 102 and the trigger 126 is described in detail below with reference to FIGS. 8, 9, 10A, and 10B.

The knife 102 is centrally disposed within the elongated shaft 116 between the interior sidewalls 162a, 162b of the outer shaft member 160 to provide lateral support to the knife 102. Free motion of the knife 102 is permitted only in a longitudinal direction. Thus, the outer shaft member 160 serves as a knife guide by urging the knife 102 into a central position within the elongated shaft 116 and, thus, ensuring proper alignment of the knife 102 as the knife 102 reciprocates within knife channel 158 (FIG. 2A). The outer shaft member 160 may also serve to protect the knife 102 and other components from damage throughout the assembly of the elongated shaft 116 and jaw members 130, 132.

Figure 4:
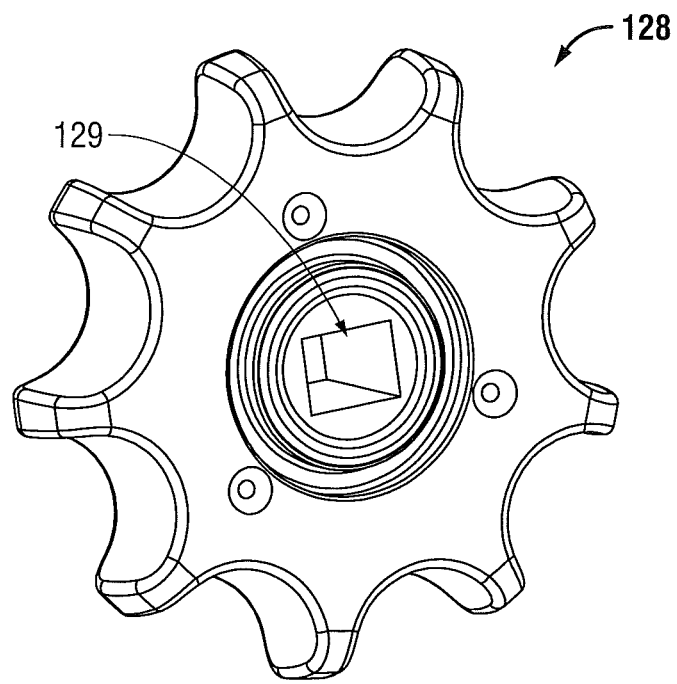
FIG. 4 is a proximally-facing perspective view of a rotation knob depicting a cavity for receiving the elongated shaft of FIG. 1.
Figure 9:
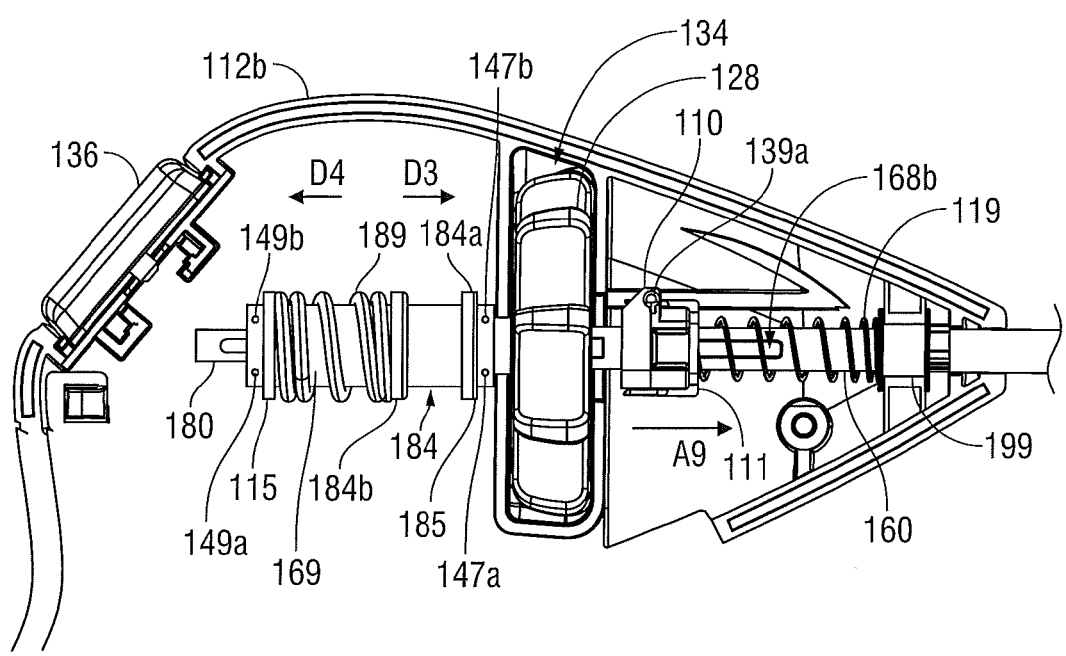
FIG. 9 is a partial, side view of a proximal portion of the instrument of FIG. 1 with a portion of the housing removed revealing internal components.

With reference to FIG. 4, the rotation knob 128 includes a passageway 129 defined therethrough for receiving the outer shaft member 160. The passageway 129 has a generally rectangular profile corresponding to the rectangular profile of the outer shaft member 160. As shown in FIG. 9, the rotation knob 128 is seated within an interior compartment 134 of the housing 112 and, as shown in FIG. 1, extends laterally outward from opposing sides of the housing 112 (only shown extending laterally outward from housing half 112b).

With reference to FIG. 5, the pivot pin 144 is coupled to the sidewalls 164a and 164b of the opening 164 defined at the distal end of the inner shaft member 180. Thus, the pivot pin 144 represents a longitudinally stationary reference for the longitudinal movements of outer shaft member 160. Laterally inward of the sidewalls 164a, 164b, the pivot pin 144 extends through the proximal end of the upper jaw member 130. Jaw member 130 is free to pivot about the pivot pin 144, and the knife 102 is free to translate longitudinally around the pivot pin 144. Inner shaft member 180 exhibits a generally U-shaped profile including exterior sidewalls 182a, 182b. Inner shaft member 180 is disposed axially within outer shaft member 160 such that exterior sidewalls 182a, 182b are disposed laterally outward from the interior sidewalls 162a, 162b of the outer shaft member 160.

Figure 6:
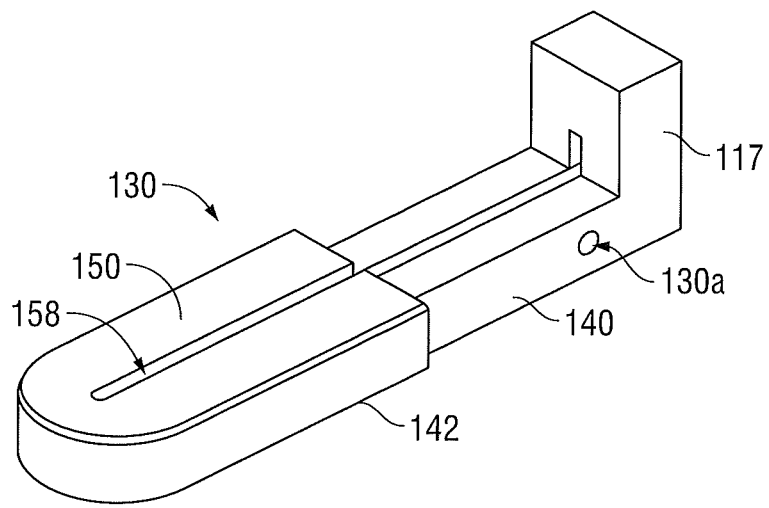
FIG. 6 is a perspective view of a lower jaw member of the end effector of FIG. 1 depicting a double flag at a proximal end thereof.
Figure 7:
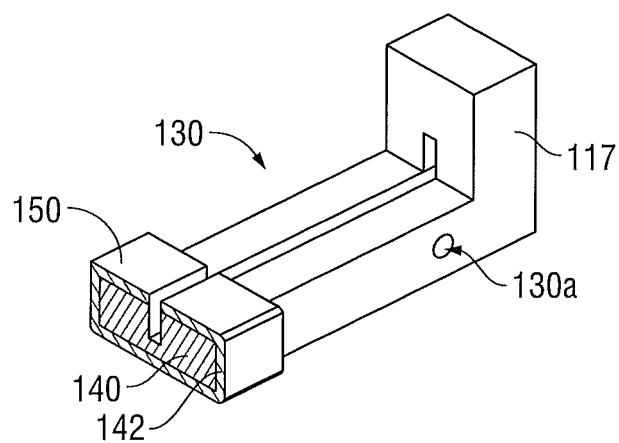
FIG. 7 is a cross-sectional, perspective view of the lower jaw member of FIG. 6.

Referring to FIGS. 6 and 7, the upper jaw member 130 is constructed of a jaw insert 140, an insulator 142, and the sealing plate 150. The insulator 142 may be constructed of an electrically insulative plastic such as a polyphthalamide (PPA) (e.g., AMODEL®), polycarbonate (PC), acrylonitrile butadiene styrene (ABS), a blend of PC and ABS, nylon, ceramic, etc. The electrically insulative plastic may be over-molded onto the jaw insert 140 in a single-shot injection molding process such that sealing plate 150 is overmolded to the jaw insert 140. Additionally or alternatively, the electrically insulative plastic may be mechanically coupled to the jaw insert 140, e.g., pressed, snapped, glued, etc. Various features may be molded into the insulator 142 that facilitate the attachment of the sealing plate 150 to the insert 140. For example, tabs may be provided that permit a snap-fit attachment of the sealing plate 150, or ridges may formed that permit ultrasonic welding of the sealing plate 150 onto the insulator 142. The sealing plate 150 may be constructed of an electrically conductive metal, and may be stamped from a flat sheet stock. Lower jaw member 132 includes the same four major components as upper jaw 130, including sealing plate 148, and is constructed in the same manner as upper jaw member 130.

Figure 8:
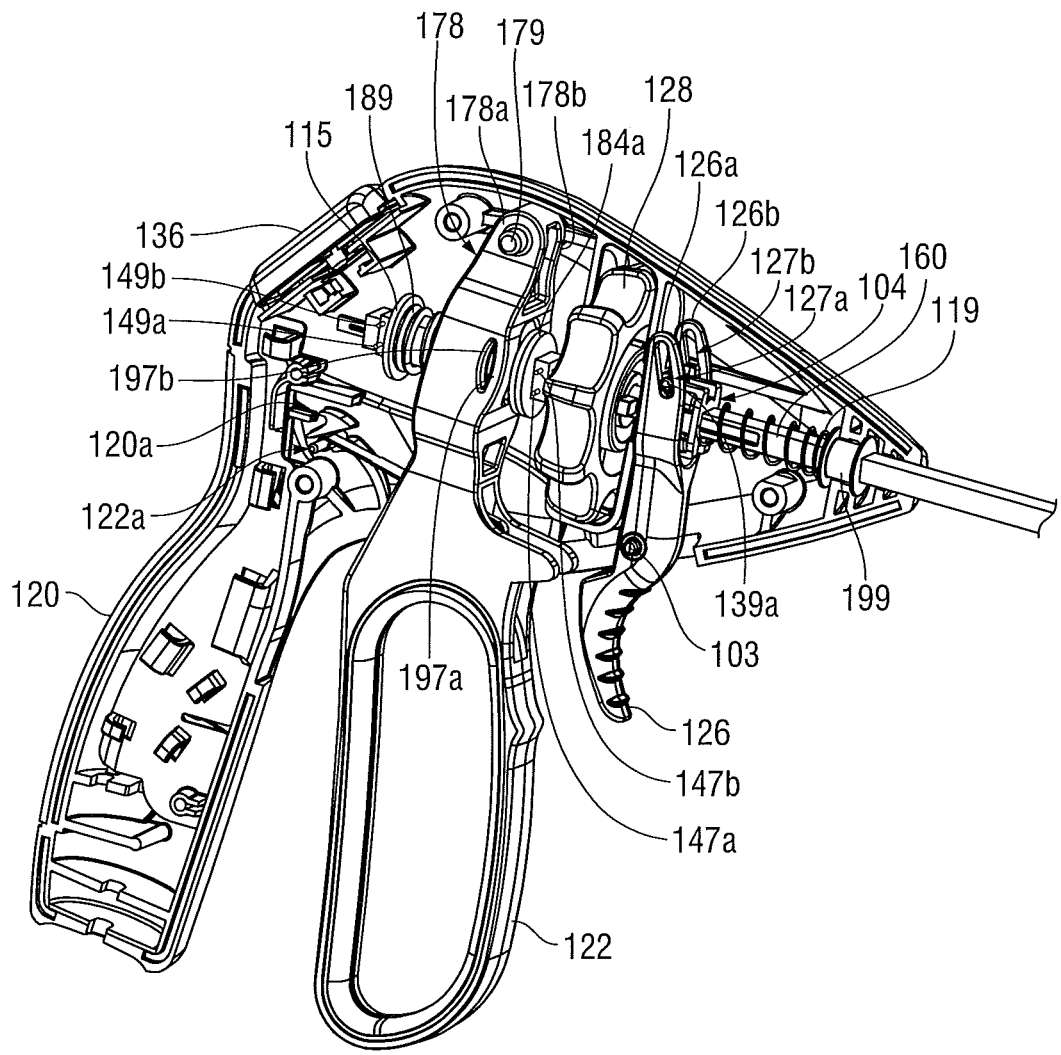
FIG. 8 is a perspective view of a proximal portion of the instrument of FIG. 1 with a portion of the housing removed revealing internal components.

Referring now to FIG. 8, the connection of the movable handle 122 and the knife trigger 126 to the longitudinally movable components of the elongated shaft 116 is described. The movable handle 122 may be manipulated to impart longitudinal motion to the outer shaft member 160, and the knife trigger 126 may be manipulated to impart longitudinal motion to the knife 102. As discussed above, longitudinal motion of the outer shaft member 160 serves to move the end effector 114 between the open configuration of FIG. 2A and the closed configuration of FIG. 2B, and longitudinal motion of the knife 102 serves to move knife blade 156 through knife channel 158 (FIG. 2A).

A clevis 178 is defined at an upper end of the movable handle 122 and is pivotally supported on the left housing half 112b by a pivot boss 179. A second complementary pivot boss (not shown) is provided on the right housing half 112a to support the clevis 178. Each of two upper flanges 178a and 178b of the clevis 178 extend upwardly about opposing sides of a drive collar 184 supported on the mandrel 169 of the outer shaft member 160 and include rounded drive surfaces 197a and 197b formed thereon. Drive surface 197a engages a proximal-facing surface of a distal rim 184a of the drive collar 184 and drive surface 197b engages a distal facing surface of a proximal rim 184b (FIG. 9) of the drive collar 184. A proximal lock washer 185 is supported on the mandrel 169 proximal of the drive collar 184 and a distal lock washer 186 is coupled to the mandrel 169 proximal to the stop pins 147a, 147b such that the stop pins 147a, 147b restrict longitudinal movement in the distal direction of the distal lock washer 186 relative to the outer shaft member 160. Drive surface 197a is arranged along the longitudinal axis A-A such that pivotal motion of the movable handle 122 about the pivot bosses 179 induces corresponding longitudinal motion of the drive collar 184 along the longitudinal axis A-A in the proximal direction. Drive surface 197b is arranged along the longitudinal axis A-A such that pivotal motion of the movable handle 122 about the pivot bosses 179 induces corresponding longitudinal motion of the drive collar 184 along the longitudinal axis A-A in the distal direction.

Referring now to FIG. 9, proximal longitudinal motion may be imparted to the outer shaft member 160 by pushing the proximal collar 184b proximally with the movable handle 122 (FIG. 8) as indicated by arrow D4. The proximal collar 184b engages a spring 189 that is constrained between the proximal collar 184b and a proximal lock collar 115. The proximal lock collar 115 engages the mandrel 169 of the outer shaft member 160 distal to the stop pins 149a, 149b. Thus, the stop pins 149a, 149b restrict longitudinal movement in the distal direction of the lock collar 115 relative to the outer shaft member 160 such that the lock collar 115 serves as a proximal stop against which spring 189 compresses.

Distal longitudinal motion is imparted to the inner shaft member 180 by pushing the distal lock collar 184a distally with drive surface 197a of movable handle 122 as indicated by arrow D3 (FIG. 9). Distal longitudinal motion of the distal lock collar 184a induces a corresponding distal motion of the outer shaft member 160 by virtue of the coupling of the distal lock collar 184a to the mandrel 169 of the outer shaft member 160.

Proximal longitudinal motion of the outer shaft member 160 draws the foot 117 proximally to pivot jaw member 130 toward jaw member 132 to move the end effector 114 to the closed configuration (FIG. 2B). Once the jaw members 130 and 132 are closed, further proximal movement of the outer shaft member 160 is prohibited since the jaw members 130, 132 contact one another. Further proximal movement of the movable handle 122 (FIG. 8), however, will continue to move the drive collar 184 proximally. This continued proximal movement of the drive collar 184 further compresses the spring 189 to impart additional force to the outer shaft member 160, which results in additional closure force applied to tissue grasped between the jaw members 130, 132.

Referring again to FIG. 8, the trigger 126 is pivotally supported in the housing 112 about a pivot boss 103 protruding from the trigger 126. The trigger 126 is operatively coupled to the knife 102 by a knife connection mechanism 104 such that pivotal motion of the trigger 126 induces longitudinal motion of the knife 102. The knife connection mechanism 104 includes upper flanges 126a, 126b of the trigger 126 and a knife collar 110.

Figures 10A, 10B:
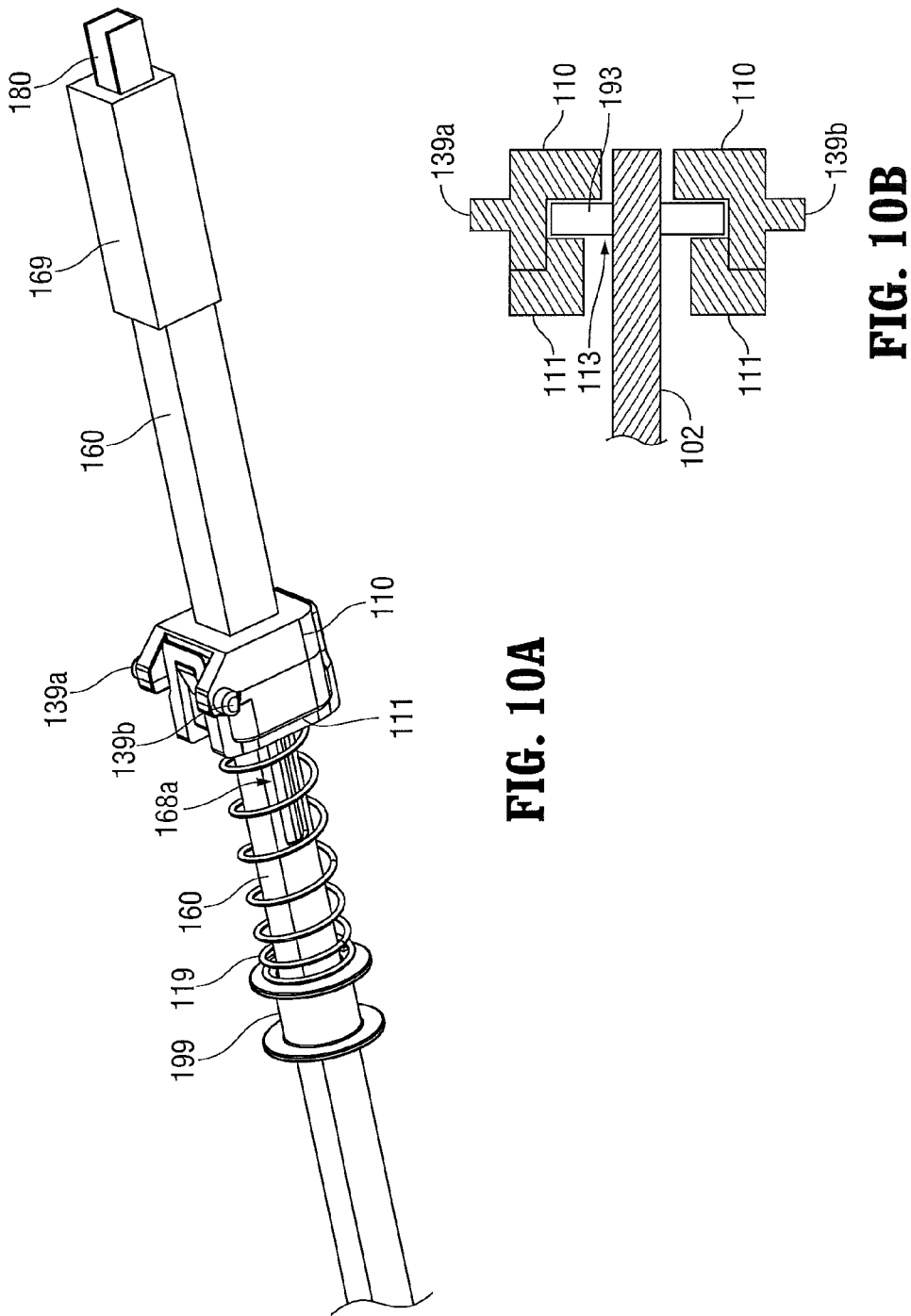
FIG. 10A is a perspective view of a proximal portion of the knife actuation mechanism of the end effector of FIG. 1.
FIG. 10B is a cross-sectional, top view of a knife collar of the knife actuation mechanism of the end effector of FIG. 1.

Referring now to FIGS. 9, 10A, and 10B, the knife collar 110 includes a cap member 111 coupled thereto and a pair of integrally formed pin bosses 139a, 139b extending from opposing sides thereof. The knife collar 110 may include indentations or catches defined therein (not shown) that receive corresponding snap-in features (e.g., arms) of the cap member 111. The cap 111 may thus be assembled to the knife collar 110 such that the cap 111 and the knife collar 110 translate together. As shown by FIG. 10B, the coupling of the knife collar 110 to the cap 111 forms an interior circular channel 113 to capture the dowel pin 193 therein such that the dowel pin 193 is supported on opposing ends between the knife collar 110 and the cap 111. The dowel pin 193 extends through the proximal through bore 108a extending through the proximal portion 108 of the knife 102 (FIG. 3) to operably couple the knife 102 to the knife collar 110. Upon longitudinal motion of the outer shaft member 160, dowel pin 193 translates longitudinally within slots 188a, 188b of the inner shaft member 180 and slots 168a, 168b of the outer shaft member 160 such that the longitudinal motion of outer shaft member 160 is unimpeded by dowel pin 193. Upon rotation of the elongated shaft 116 and end effector 114 about the longitudinal axis A-A via the rotation knob 128 (FIG. 1), dowel pin 193 freely rotates within the interior circular channel 113 such that the outer and inner shaft members 160 and 180 (removed from view in FIG. 10B for clarity), the knife 102, and the dowel pin 193 rotate within the knife collar 110 about the longitudinal axis A-A.

Referring again to FIG. 8, the upper flanges 126a, 126b of the trigger 126 include respective slots 127a, 127b defined therethrough that are configured to receive the pin bosses 139a, 139b, respectively, of the knife collar 110 such that pivotal motion of the trigger 126 induces longitudinal motion of the knife collar 110 and, thus, the knife 102 by virtue of the coupling of knife 102 to the knife collar 110 via the dowel pin 193 extending through the through bore 108a. During longitudinal motion of the knife collar 110, dowel pin 193 translates longitudinally within the opposing slots 168a, 168b of the outer shaft member 160 and the slots 188a, 188b of the inner shaft member 180.

Referring now to FIGS. 9 and 10A, when the trigger 126 is moved to induce motion of the knife collar 110 in order to translate the blade 156 through the knife channel 158, the knife collar 110 translates along the outer shaft member 160 in the direction of arrow A9 to abut a spring 119 such that spring 119 compresses against a bobbin 199 disposed within the interior of the housing 112. The spring 119 biases the knife collar 110 in a proximal direction to a proximal position along the outer shaft member 160.

Figure 11B:
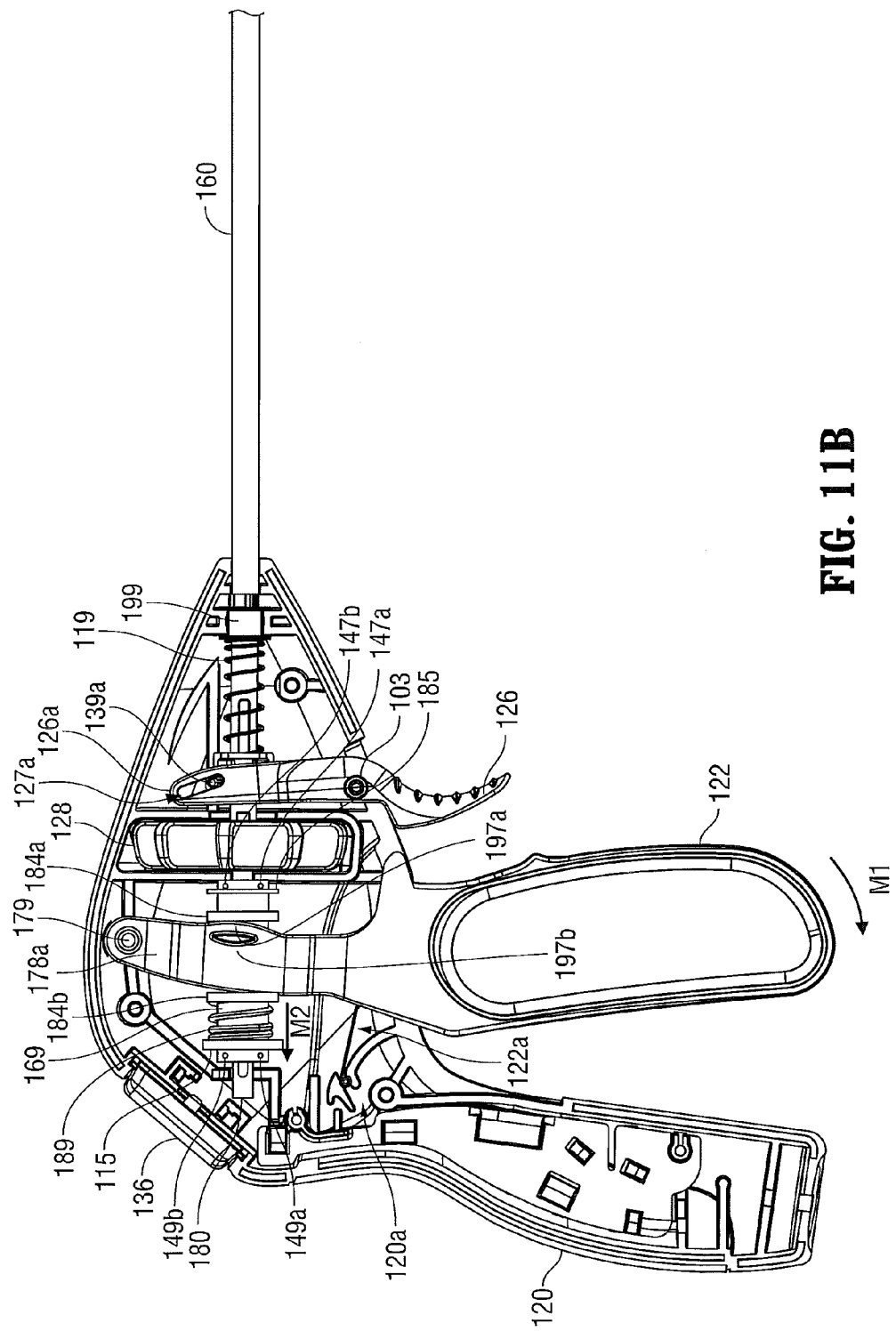
FIG. 11B is a side view of the proximal portion of the instrument of FIG. 8 depicting the movable handle in an intermediate position with respect to the stationary handle, which corresponds to a first closed configuration of the end effector wherein the jaw members encounter one another.

Referring now to FIGS. 11A, 11B, 11C and 11D, a sequence of motions may be initiated by moving the movable handle 122 to induce motion of the outer shaft member 160 in order to close the jaw members 130, 132, and by moving the trigger 126 to induce motion of the knife collar 110 in order to translate the blade 156 through the knife channel 158. Initially, both the moveable handle 122 and the knife trigger 126 are in a distal or un-actuated position as depicted in FIG. 11A. This arrangement of the moveable handle 122 and trigger 126 sustains the end effector 114 in the open configuration (FIG. 2A) wherein the jaw members 130, 132 are substantially spaced from one another, and the knife blade 156 is in a retracted or proximal position with respect to the jaw members 130, 132. The initial distal position of the trigger 122 is actively maintained by the influence of the spring 119 on the knife collar 110. When both the moveable handle 122 and the knife trigger 126 are in the distal, un-actuated position, pivotal motion of the knife trigger 126 in a proximal direction, i.e., toward the stationary handle 120, is prohibited by interference between the trigger 126 and moveable handle 122. This interference prohibits advancement of the knife blade 156 through the knife channel 158 when the end effector 114 is in the open configuration.

The movable handle 122 may be moved from the distal position of FIG. 15A to the intermediate position depicted in FIG. 15B to move the jaw members 130, 132 to the closed configuration (FIG. 2B). As the movable handle 122 pivots about the pivot boss 179 in the direction of arrow M1 (FIG. 11B), the drive surface 197b of the movable handle 122 engages the proximal collar 184b. The drive collar 184 and the spring 189 are both driven proximally against the proximal lock collar 115 and, thus, the outer shaft member 160 is driven proximally in the direction of arrow M2 (FIG. 11B). Proximal movement of the outer shaft member 160 serves to pivot jaw member 130 toward jaw member 132.

Figure 11C:
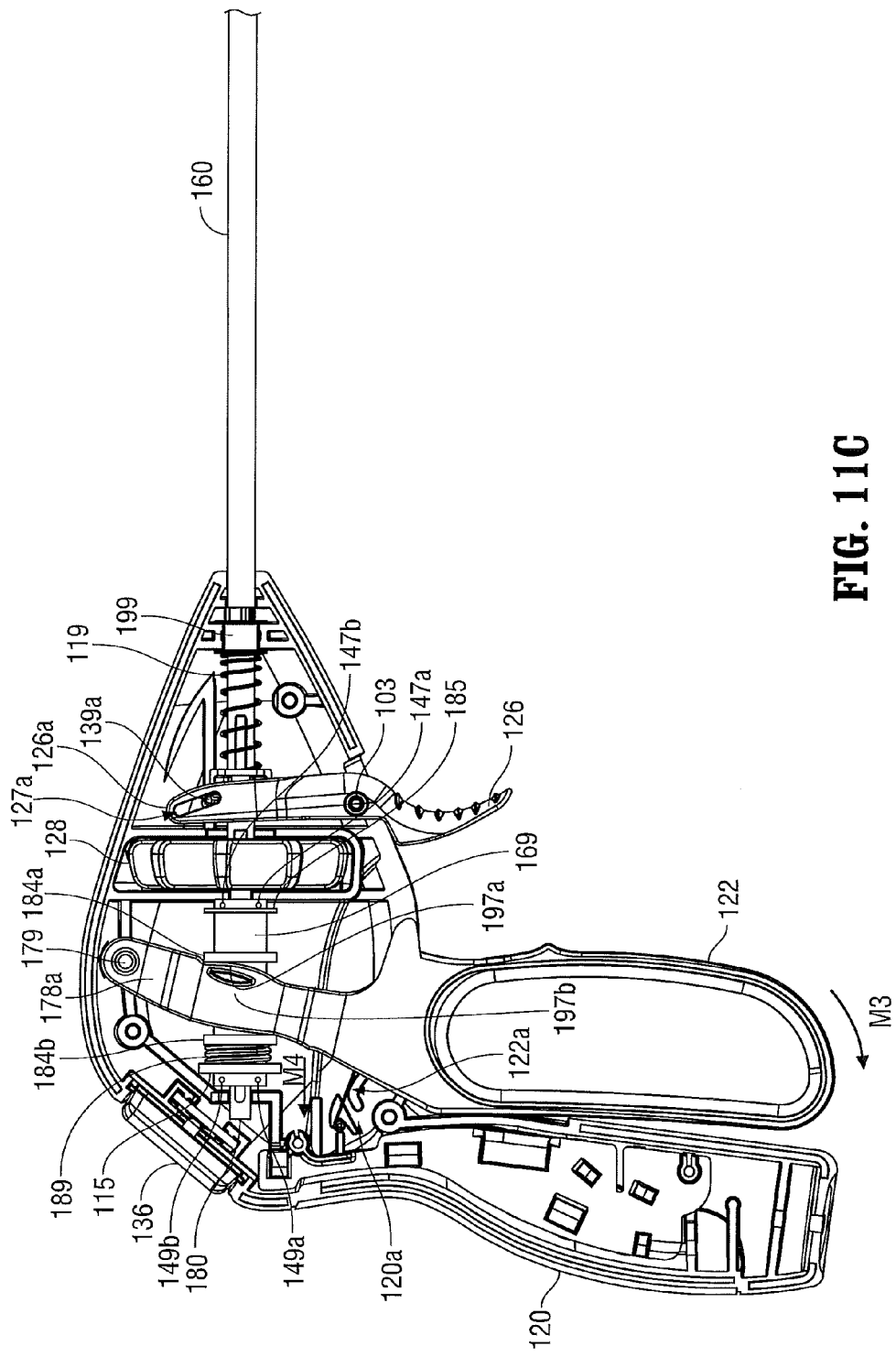
FIG. 11C is a side view of the proximal portion of the instrument of FIG. 8 depicting the movable handle in an approximated configuration with respect to the stationary handle, which corresponds to a second closed configuration of the end effector wherein the jaw members apply an appropriate pressure to generate a tissue seal.

The movable handle 122 may be moved from the intermediate position of FIG. 15B to the actuated or proximal position of FIG. 11C to increase the pressure applied by the jaw members 130, 132. As the movable handle 122 pivots further about the pivot boss 179 in the direction of arrow M3 (FIG. 11C), the drive surface 197b presses the proximal collar 184b further distally against the spring 189 in the direction of arrow M4 (FIG. 11C). The spring 189 is compressed against the proximal lock collar 115, and a tensile force is transmitted through the outer shaft member 160 to the jaw members 130, 132. The tensile force supplied by the spring 189 ensures that the jaw members 130, 132 apply an appropriate pressure to effect a tissue seal. When the movable handle 122 is in the actuated or proximal position, electrosurgical energy may be selectively supplied to the end effector 114 to generate a tissue seal.

When the movable handle 122 is in the actuated or proximal position, a t-shaped latch 122a extending proximally from an upper portion of the moveable handle 122 is received in a railway 120a supported within the stationary handle 120. The railway 120a serves to temporarily lock the movable handle 122 in the proximal position against the bias of the spring 189. Thus, the railway 120a permits the maintenance of pressure at the end effector 114 without actively maintaining pressure on the movable handle 122. The latch 122a may be released from the railway 121a by pivoting the movable handle 122 proximally and releasing the movable handle 122 to move under the influence of the spring 189. Operation of the railway 120a is described in greater detail in U.S. patent application Ser. No. 11/595,194 to Hixson et al., now U.S. Pat. No. 7,766,910. In some embodiments (not shown), the latch 122a and the railway 120a may be eliminated to provide an instrument without the temporary locking capability provided by these features.

Figure 11D:
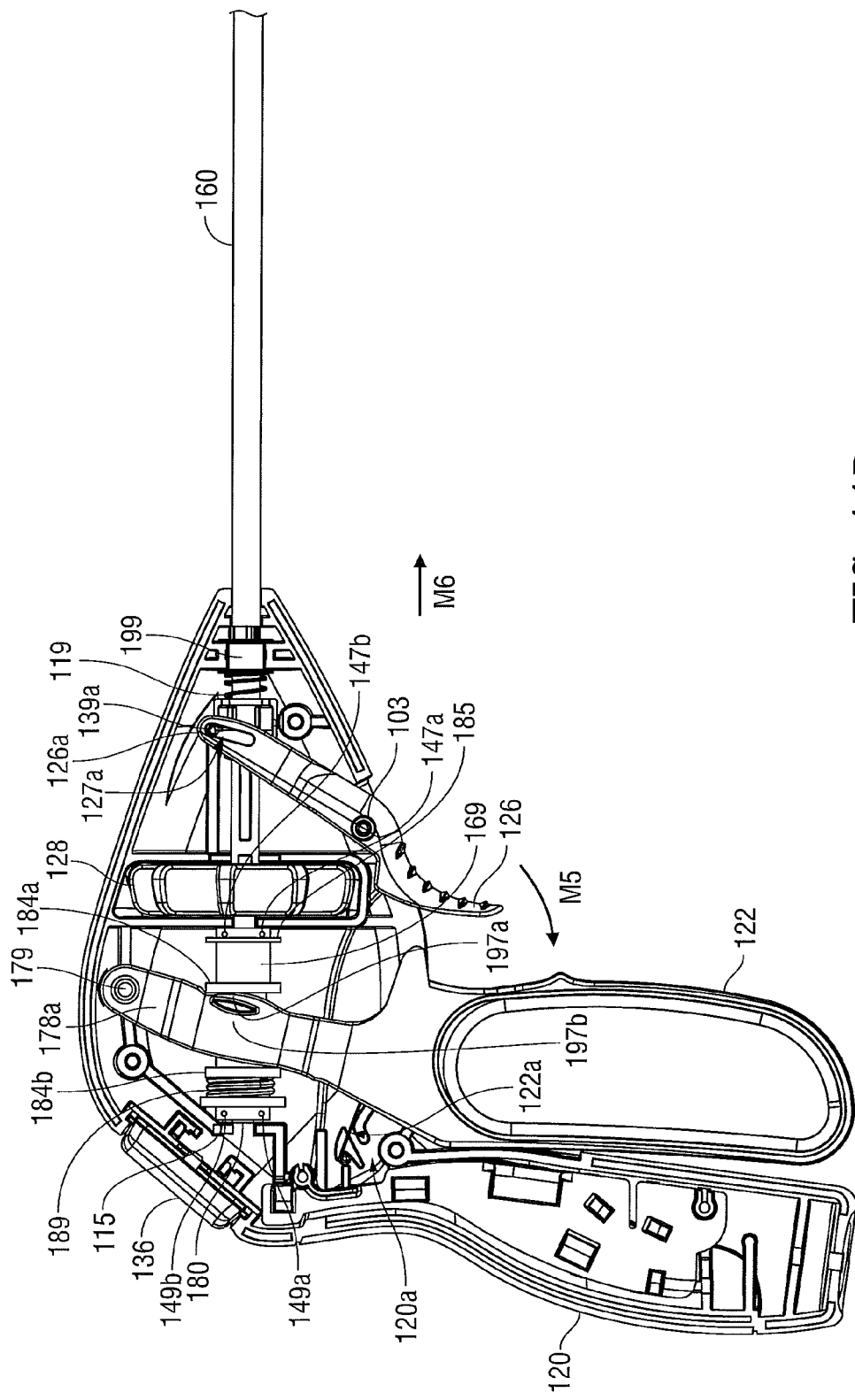
FIG. 11D is a side view of the proximal portion of the instrument of FIG. 8 depicting the knife trigger in an actuated configuration, which corresponds to an actuated or distal position of the knife with respect to the jaw members.

When the movable handle 122 is in the actuated or proximal position, the knife trigger 126 may be selectively moved from the distal position of FIG. 11C to the proximal position of FIG. 11D to advance the knife blade 156 distally through knife channel 158. The knife trigger 126 may be pivoted in the direction of arrow M5 (FIG. 11D), about pivot boss 103 to advance the flanges 126a, 126b of the knife trigger 126 distally in the direction of arrow M6 such that the pin bosses 139a, 139b translate within slots 127a, 127b, respectively, from the position shown in FIGS. 11A-11C to the position shown in FIG. 11D. Movement of flanges 126a, 126b draws the knife collar 110 distally, which induces distal longitudinal motion of the knife 102 by virtue of the coupling of knife 102 to the knife collar 110 via the dowel pin 193 extending through the through bore 108a, as described above with reference to FIGS. 3 and 10B.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. A surgical instrument, comprising:
   a housing including an elongated shaft having a distal portion and a proximal portion coupled to the housing, the elongated shaft defining a longitudinal axis and a mandrel at the proximal portion, the elongated shaft having a generally u-shaped profile including opposing interior sidewalls, the elongated shaft stamped from a single piece of metal;
   an inner shaft member extending at least partially through the elongated shaft;
   an actuating mechanism operably coupled to the mandrel and configured to selectively cause movement of the elongated shaft in a longitudinal direction with respect to the inner shaft member;
   an end effector adapted for treating tissue and including an upper jaw member pivotally coupled to a distal portion of the inner shaft member about a pivot axis and a lower jaw member supported by the distal portion of the elongated shaft, the elongated shaft configured to pivot the upper jaw member relative to the lower jaw member upon longitudinal movement relative to the inner shaft member; and
   a knife extending at least partially through the elongated shaft between the opposing interior sidewalls and selectively movable in a longitudinal direction, the knife including a blade extendable through a tissue contacting portion of the jaw members.

2. The surgical instrument according to claim 1, wherein the knife is stamped from a single piece of metal.

3. The surgical instrument according to claim 1, wherein the inner shaft member is stamped from a single piece of metal.

4. The surgical instrument according to claim 1, wherein the upper jaw member includes a foot extending therefrom configured to engage the elongated shaft, wherein proximal longitudinal motion of the elongated shaft biases the foot proximally to pivot the upper jaw member toward the lower jaw member and distal longitudinal motion of the elongated shaft biases the foot distally to pivot the upper jaw member away from the lower jaw member.

5. A surgical instrument, comprising:
   a housing including an elongated shaft having a distal portion and a proximal portion coupled to the housing, the elongated shaft defining a longitudinal axis and a mandrel at the proximal portion, the elongated shaft having a generally u-shaped profile including opposing interior sidewalls;
   an inner shaft member extending at least partially through the elongated shaft, the inner shaft stamped from a single piece of metal;
   an actuating mechanism operably coupled to the mandrel and configured to selectively cause movement of the elongated shaft in a longitudinal direction with respect to the inner shaft member;
   an end effector adapted for treating tissue and including an upper jaw member pivotally coupled to a distal portion of the inner shaft member about a pivot axis and a lower jaw member supported by the distal portion of the elongated shaft, the elongated shaft configured to pivot the upper jaw member relative to the lower jaw member upon longitudinal movement relative to the inner shaft member; and
   a knife extending at least partially through the elongated shaft between the opposing interior sidewalls and selectively movable in a longitudinal direction, the knife including a blade extendable through a tissue contacting portion of the jaw members.

* * * * *